(12) United States Patent
Lee et al.

(10) Patent No.: US 11,524,182 B2
(45) Date of Patent: Dec. 13, 2022

(54) NON-INVASIVE TREATMENT SYSTEM USING INTERMEDIUM

(71) Applicant: KOREA INSTITUTE OF SCIENCE AND TECHNOLOGY, Seoul (KR)

(72) Inventors: Byung Chul Lee, Seoul (KR); Hyung Min Kim, Seoul (KR); Ki Joo Pahk, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 311 days.

(21) Appl. No.: 16/276,396

(22) Filed: Feb. 14, 2019

(65) Prior Publication Data

US 2020/0121959 A1 Apr. 23, 2020

(30) Foreign Application Priority Data

Oct. 18, 2018 (KR) .......................... 10-2018-0124429

(51) Int. Cl.
*A61N 7/02* (2006.01)
*A61N 7/00* (2006.01)

(52) U.S. Cl.
CPC .......... *A61N 7/02* (2013.01); *A61N 2007/0004* (2013.01); *A61N 2007/0052* (2013.01);
(Continued)

(58) Field of Classification Search
CPC ........ A61B 17/2251; A61B 2017/2253; A61N 2007/0004; A61N 2007/0026;
(Continued)

(56) References Cited

U.S. PATENT DOCUMENTS 9,044,195 B2 6/2015 Manwaring et al.
2006/0052707 A1* 3/2006 Dickinson ............ A61B 8/4488
600/466

(Continued)

FOREIGN PATENT DOCUMENTS

KR 10-2011-0011914 A 2/2011

OTHER PUBLICATIONS

Damestani et al., "Transparent nanocrystalline yttria-stabilized-zirconia calvarium prosthesis", Nanomedicine: Nanotechnology, Biology, and Medicine, 2013, vol. 9, pp. 1135-1138.
(Continued)

*Primary Examiner* — Yi-Shan Yang
*Assistant Examiner* — Alexei Bykhovski
(74) *Attorney, Agent, or Firm* — Birch, Stewart, Kolasch & Birch, LLP

(57) ABSTRACT

Disclosed herein is a non-invasive treatment system using intermedium, and an exemplary treatment system is configured to output high-intensity focused ultrasound to remove bone tissue, inject an acoustically-transparent medium into a part where the bone tissue is removed to generate an intermedium, and output therapeutic ultrasound that passes through the intermedium. Accordingly, the bone tissue is removed in a non-invasive way using high-intensity focused ultrasound, and the intermedium is generated at the bone tissue removed site, to increase the penetration of therapeutic ultrasound or generate ultrasound itself, thereby improving an ultrasound treatment effect while minimizing the side effect (for example, infection of dura mater) of invasive surgery methods.

17 Claims, 11 Drawing Sheets

(52) U.S. Cl.
CPC ................ *A61N 2007/0056* (2013.01); *A61N 2007/0078* (2013.01)

(58) Field of Classification Search
CPC .... A61N 2007/0052; A61N 2007/0056; A61N 2007/0078; A61N 7/02
See application file for complete search history.

(56) References Cited

U.S. PATENT DOCUMENTS

| | | |
|---|---|---|
| 2007/0129652 A1 | 6/2007 | Nita |
| 2007/0185231 A1* | 8/2007 | Liu ..................... A61L 24/0005 |
| | | 523/116 |
| 2009/0099485 A1* | 4/2009 | Sarvazyan ............... A61N 7/00 |
| | | 601/2 |
| 2011/0028867 A1 | 2/2011 | Choo et al. |
| 2012/0083717 A1 | 4/2012 | Alleman et al. |
| 2013/0204316 A1 | 8/2013 | Carpentier et al. |
| 2015/0151142 A1 | 6/2015 | Tyler et al. |
| 2018/0177491 A1* | 6/2018 | Hynynen ............... A61B 34/10 |
| 2018/0310831 A1* | 11/2018 | Cheng .................. A61B 5/6851 |

OTHER PUBLICATIONS

Gutierrez et al., "Novel Cranial Implants of Yttria-Stabilized Zirconia as Acoustic Windows for Ultrasonic Brain Therapy", Advanced Healthcare Materials, 2017, vol. 6, No. 1700214, total of 11 pages.

* cited by examiner

NON-INVASIVE TREATMENT SYSTEM USING INTERMEDIUM

DESCRIPTION OF GOVERNMENT-SPONSORED RESEARCH

This research is done in support of study-centered hospital advancement program (Development of non-invasive ultrasound based neuromodulation and muscle rehabilitation system, Project series number: 1465026068) of Ministry of Health and Welfare under the supervision of Korea Institute of Science and Technology, and in support of the Bio & Medical Technology Development Program (Commercialization research of micromachined ultrasonic transducers and their attachable devices, Grant No.: 2018M3A9G5075746) of National Research Foundation (NRF) by the Ministry of Science and ICT under the supervision of Korea Institute of Science and Technology.

CROSS-REFERENCE TO RELATED APPLICATION

This application claims priority to Korean Patent Application No. 10-2018-0124429, filed on Oct. 18, 2018, and all the benefits accruing therefrom under 35 U.S.C. § 119, the contents of which in its entirety are herein incorporated by reference.

BACKGROUND

1. Field

The present disclosure relates to a non-invasive treatment system using intermedium, and more particularly, to a non-invasive treatment system for improving an ultrasound treatment effect by generating an acoustically-transparent intermedium at a part where the bone tissue is removed using high-intensity focused ultrasound.

2. Description of the Related Art

To conduct therapy that mitigates a patient's pain or stimulates neural cells in a specific human body part, a method that inserts electrodes into the patients body has been used, but there is a risk that the body may be damaged by this physical invasion process.

Recently, ultrasound stimulation therapy that can stimulate an affected part without a physical invasion process is widely used. Ultrasound may be classified into High-intensity Focused Ultrasound (HIFU) and Low-intensity Focused Ultrasound (LIFU) according to the intensity, and it is known that high-intensity focused ultrasound is used for direct treatment, for example, necrosis of human body tissues such as cancer cells, tumors and lesions, while low-intensity focused ultrasound can obtain medical effects without necrotizing human body tissues.

The unit of ultrasound intensity is indicated by spatial-peak temporal-average intensity (Ispta) and spatial-peak pulse average intensity (Isppa) according to the Acoustic Output Measurement Standard for Diagnostic Ultrasound Equipment by American Institute for Ultrasound in Medicine and National Electronics Manufacturers Administration (NEMA).

The standard for the type of ultrasound is not yet explicitly defined, but in general, according to U.S. FDA standards and European Safety standards, "low intensity ultrasound" is ultrasound having the spatial-peak temporal-average intensity (Ispta) of less than 3 W/cm$^2$ and refers to ultrasound within a range in which the human body is not damaged, and ultrasound having the spatial-peak temporal-average intensity of 3 W/cm$^2$ or above may be classified as "high intensity ultrasound".

Recently, medical technology is used, which treats neurological disorders such as cognitive impairment, anxiety and depression in a non-invasive way by stimulating a patient's brain with low-intensity focused ultrasound (LIFU), or removes lesions in a non-invasive way by use of high-intensity focused ultrasound (HIFU).

In the therapy that stimulates the patient's brain or removes the lesion with focused ultrasound, the problem with reduced ultrasound treatment effect due to the structure of the skull has been raised. Referring to FIG. 1, for treatment, ultrasound needs to reach the brain through the skull, but because the skull has a porous structure, ultrasound bounds off the surface and attenuation occurs. In particular, there is a greater difficulty in using high frequency ultrasound for imaging due to a greater influence of the porous structure of the skull as the frequency of ultrasound is higher.

To solve the above-described problem, technology has been developed that incises part of a patient's skull, and inserts an acoustic window into the corresponding part to increase the penetration of ultrasound for treatment.

However, the above-described method has a risk that the dura mater surrounding the brain may be infected during incision of the patient's skull, and thus it is not suitable for non-invasive therapy using ultrasound.

SUMMARY

The present disclosure is directed to providing a method that removes bone tissue by a non-invasive method and forms an acoustically-transparent intermedium at the site where the bone tissue is removed to prevent the side effect such as infection caused by a surgery involving incision of the skull by an invasive method, thereby improving the penetration of therapeutic ultrasound together with minimizing invasion.

A non-invasive treatment system using intermedium according to an embodiment of the present disclosure is configured to output high-intensity focused ultrasound to remove bone tissue, inject an acoustically-transparent medium into a part where the bone tissue is removed to generate an intermedium, and output therapeutic ultrasound that passes through the intermedium.

In an embodiment, the therapeutic ultrasound may include high-intensity focused ultrasound (HIFU), low-intensity focused ultrasound (LIFU), or high frequency ultrasound for imaging.

In an embodiment, the intermedium may include a plurality of acoustically-transparent intermedia generated at preset locations, the plurality of acoustically-transparent intermedia may allow therapeutic ultrasound outputted from each of a plurality of ultrasound output elements to pass through, and the therapeutic ultrasound may stimulate a lesion with higher intensity through an overlap.

A non-invasive treatment system using intermedium according to another embodiment of the present disclosure is configured to output high-intensity focused ultrasound to remove bone tissue, inject a medium into a part where the bone tissue is removed to generate an intermedium that can generate ultrasound itself by external induction, and induce the intermedium to generate the ultrasound.

In an embodiment, the intermedium may be made of an opto-acoustic material that generates ultrasound by incident light, and the treatment system may be further configured to allow light to enter the intermedium.

In an embodiment, the intermedium may be made of a piezoelectric material that generates ultrasound by applied voltage, and the treatment system may be further configured to apply voltage to the intermedium.

In an embodiment, the intermedium may act as an amplifier to amplify received ultrasound, and the treatment system may be further configured to output ultrasound to the intermedium.

In an embodiment, the intermedium may be made of a ferroelectric material that generates ultrasound by a change in electromagnetic field, and the treatment system may be further configured to generate an electromagnetic field.

A non-invasive treatment device using intermedium according to an embodiment of the present disclosure includes an ultrasound output unit to output high-intensity focused ultrasound to remove bone tissue, a medium injection unit to inject a medium into a part where the bone tissue is removed to generate an intermedium, and a control unit to control operation of the ultrasound output unit.

In an embodiment, the intermedium may be made of an acoustically-transparent material, and the ultrasound output unit may further output therapeutic ultrasound that passes through the intermedium.

In an embodiment, the intermedium may include a plurality of acoustically-transparent intermedia generated at preset locations, the ultrasound output unit may include a plurality of ultrasound output elements corresponding to the plurality of acoustically-transparent intermedia, the plurality of acoustically-transparent intermedia may allow therapeutic ultrasound outputted from each of the plurality of ultrasound output elements to pass through, and the therapeutic ultrasound may stimulate a lesion with higher intensity through an overlap.

In an embodiment, the intermedium may be made of a material that can generate ultrasound itself by external induction, and the treatment device may further include an ultrasound induction unit to induce the intermedium to generate ultrasound.

In an embodiment, the intermedium may be made of an opto-acoustic material that generates ultrasound by incident light, and the ultrasound induction unit may allow light to enter the intermedium.

In an embodiment, the intermedium may be made of a piezoelectric material that generates ultrasound by applied voltage, and the ultrasound induction unit may apply voltage to the intermedium.

In an embodiment, the intermedium may act as an amplifier to amplify received ultrasound, and the ultrasound induction unit may output ultrasound to the intermedium.

In an embodiment, the intermedium may be made of a ferroelectric material that generates ultrasound by a change in electromagnetic field, and the ultrasound induction unit may generate an electromagnetic field.

In an embodiment, the ultrasound output unit may include an ultrasonic transducer using a piezoelectric material, a capacitive micromachined ultrasonic transducer (CMUT), a piezoelectric micromachined ultrasonic transducer (PMUT), an ultrasonic transducer using an opto-acoustic effect, or an ultrasonic transducer using an electromagnetic force.

Using the ultrasound treatment system according to an embodiment of the present disclosure, the bone tissue can be removed in a non-invasive way using high-intensity focused ultrasound and the acoustically-transparent intermedium can be generated at the part where the bone tissue is removed through a syringe. Accordingly, it is possible to improve the ultrasound treatment effect while minimizing the side effect (for example, infection of dura mater) of invasive surgery methods.

According to another embodiment, the intermedium generated by injecting the medium may be made of an acoustic window as well as a material that can generate ultrasound itself, such as an optoacoustic material, a piezoelectric material and a ferroelectric material, and thus can be variously used according to the purpose.

DETAILED DESCRIPTION

Hereinafter, the embodiments will be described in detail with reference to the accompanying drawings and the context described in the accompanying drawings, but the intended scope is not defined or limited by the disclosed embodiments.

The terms as used herein are general terms selected as those being now used as widely as possible in consideration of functions, but they may vary depending on the intention of those skilled in the art or the convention or the emergence of new technology. Additionally, in certain cases, there may be terms arbitrarily selected by the applicant, and in this case, the meaning will be described in the corresponding description part of the specification. Accordingly, it should be noted that the terms as used herein should be interpreted based on the substantial meaning of the terms and the context throughout the specification, rather than simply the name of the terms.

Additionally, the embodiment described herein may have aspects of entirely hardware, partly hardware and partly software, or entirely software. The term "unit", "module", "device", "server" or "system" used herein refers to computer related entity such as hardware, hardware and software in combination, or software. For example, the unit, module, device, server or system may refer to hardware that makes up a platform in part or in whole and/or software such as an application for operating the hardware.

Hereinafter, the exemplary embodiments of the present disclosure will be described in more detail with reference to the accompanying drawings.

Figure 1:
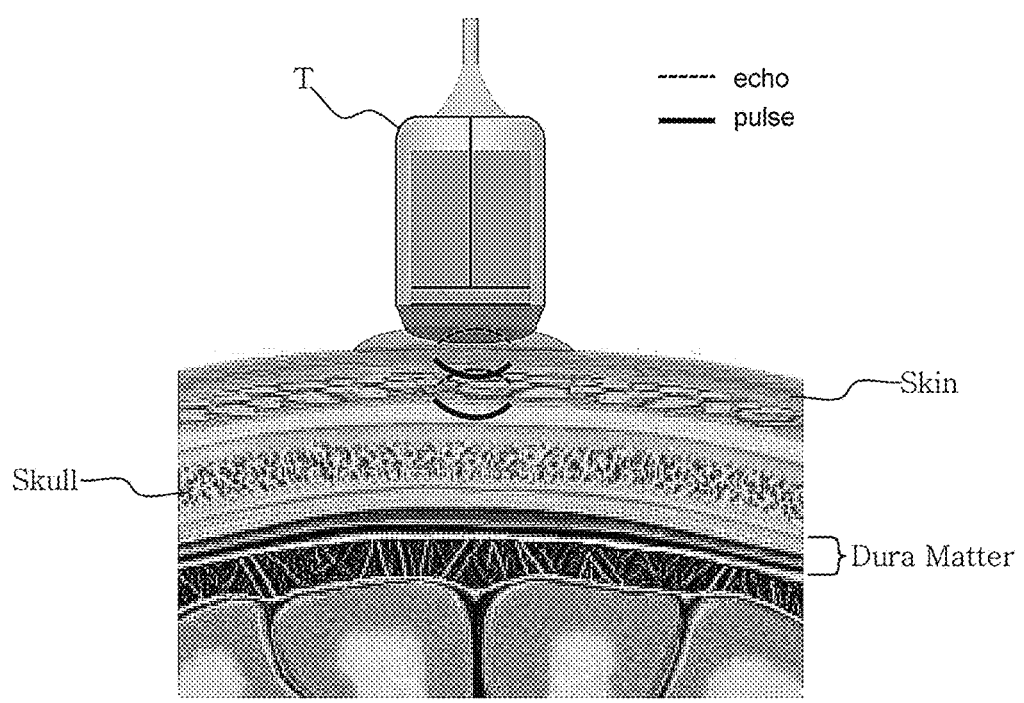
FIG. 1 shows reflection occurring in the skull when performing ultrasound treatment without intermedium.

FIG. 1 shows a problem occurring in the skull when performing ultrasound treatment without intermedium according to the related art. In therapy that stimulates a patient's brain or removes lesions with focused ultrasound, it is important that ultrasound pulses are transmitted to the brain through the skull. However, because the skull has a porous structure, ultrasound bounces off the surface and attenuation occurs. In particular, the porous structure of the skull has a greater influence as the frequency of ultrasound is higher, and thus there is difficulty in using high frequency ultrasound for imaging.

Figure 2:
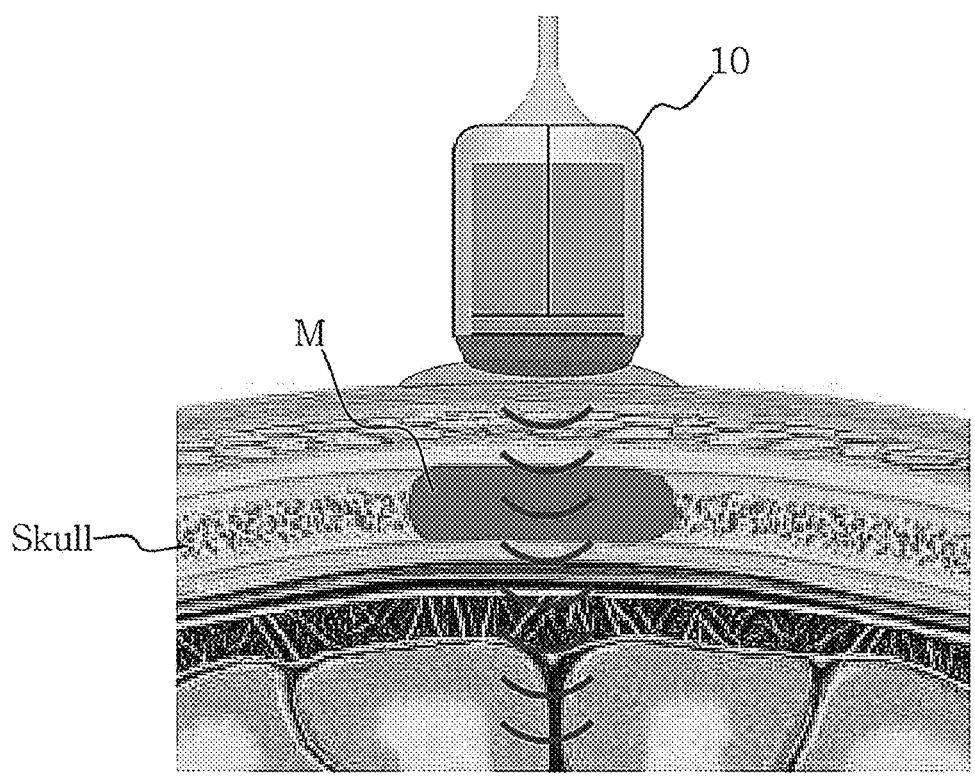
FIG. 2 shows ultrasound treatment performed after forming an acoustically-transparent intermedium in the skull according to an embodiment.

FIG. 2 shows ultrasound treatment performed after forming an intermedium M in the skull according to an embodiment, to solve the above-described problem. Here, the intermedium acts as an acoustic window to allow therapeutic ultrasound to reach the brain through the skull. To this end, the intermedium may be made of a sound permeable medium through which ultrasound can pass, such as amalgam or silicone, but this is for illustration purposes only, and the intermedium is not limited to a particular material. With the acoustically-transparent intermedium, therapeutic ultrasound outputted from an ultrasound output unit 10 may reach the brain part without attenuation.

Figure 3:
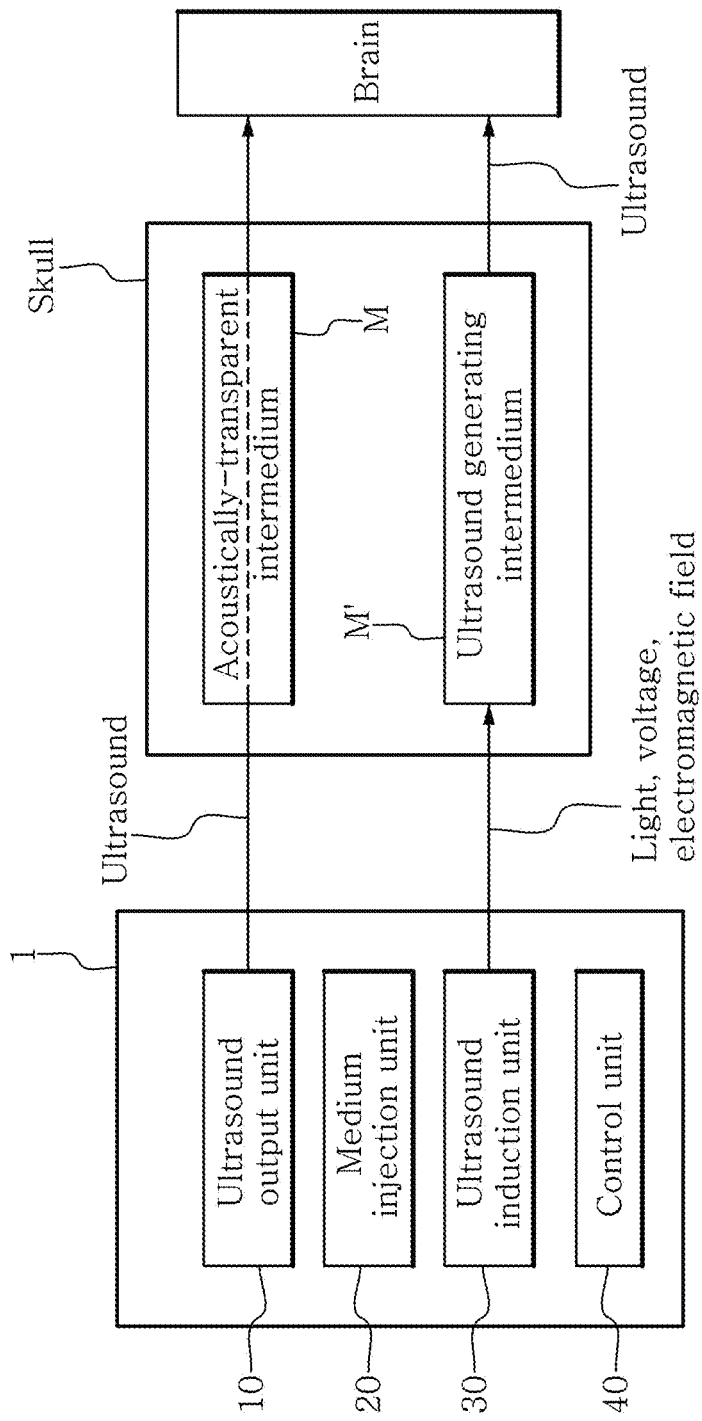
FIG. 3 is a block diagram showing an ultrasound treatment system using intermedium according to an embodiment.

FIG. 3 is a block diagram showing an ultrasound treatment system using intermedium according to an embodiment. Referring to FIG. 3, the non-invasive treatment system operates by interaction between a treatment device 1 including mechanical components, an ultrasound output unit 10, a medium injection unit 20, an ultrasound induction unit 30 and a control unit 40, and an intermedium M, M' generated in a patient's skull.

Therapeutic ultrasound outputted from the ultrasound output unit 10 may stimulate the brain through the acoustically-transparent intermedium M, or the ultrasound generating intermedium M' may generate ultrasound itself according to an input from the ultrasound induction unit 30 to stimulate the brain or capture an image. To this end, the process of forming the intermedium M or M' in the patient's skull should be performed in advance.

The ultrasound output unit 10 may output not only low intensity ultrasound of 3 W/cm² (Ispta) or less but also high intensity ultrasound of 3 W/cm² (Ispta) or above by adjusting the output according to a target part and the purpose of treatment, as a sound source that may focus ultrasound onto a target focal point desired by a user with desired intensity.

In general, an ultrasonic transducer converts the alternating current energy of 20 KHz or above to mechanical vibration of the same frequency using the piezoelectric effect or magnetostrictive effect. For example, the transducer includes a body with one open side and piezoelectric elements, the body is filled with air, and an electric wire is connected to each piezoelectric element to apply the voltage. The piezoelectric element uses a material exhibiting a piezoelectric effect such as quartz and tourmaline, and the transducer may generate and output ultrasound using the piezoelectric effect of the piezoelectric element. The structure of the transducer is provided for illustration purposes only, and the transducer is not limited to a particular structure or effect. The piezoelectric element of the transducer may output a proper intensity of ultrasound by adjusting the output according to the purpose, and the outputted ultrasound has an overlap, forming an ultrasound beam.

Here, the 'ultrasound output unit' should be understood as a concept that encompasses a single transducer device having a single focal point, as well as an array unit including a plurality of ultrasound devices arranged in one or two dimensions. Each ultrasound device may include all types of ultrasound devices, for example, an ultrasonic transducer using a piezoelectric material, a micromachined ultrasonic transducer (MUT) such as capacitive MUT (CMUT) and piezoelectric MUT (PMUT), an ultrasonic transducer using an opto-acoustic effect, and an ultrasonic transducer using an electromagnetic force.

Hereinafter, the process of generating the intermedium in the skull will be described with reference to FIGS. 4A to 4C.

Figure 4A:
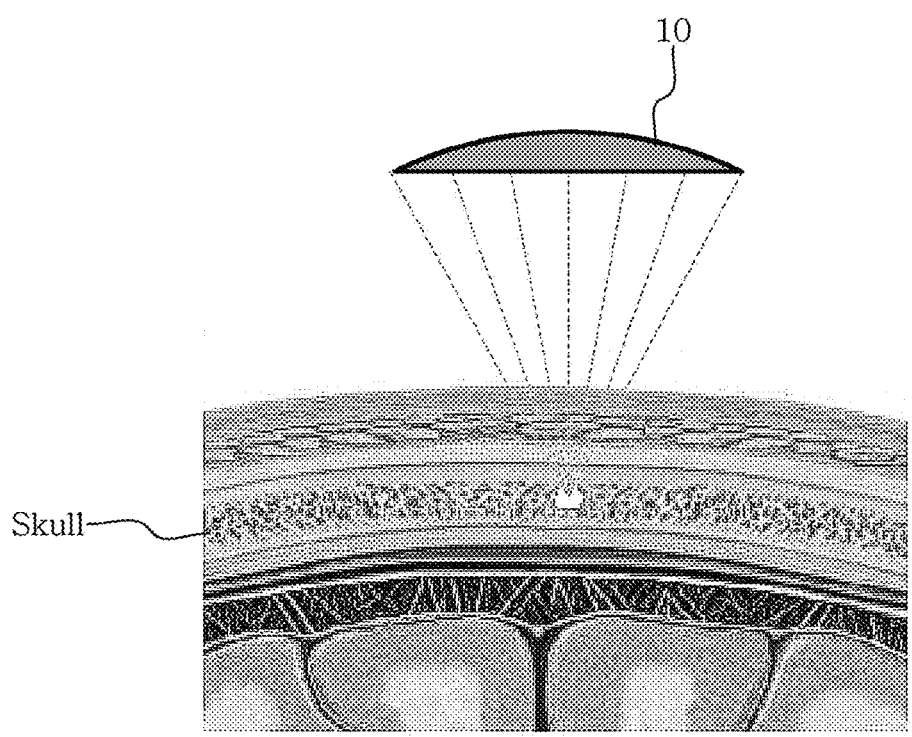
FIGS. 4A to 4C show a process of generating an intermedium in the skull according to an embodiment.

As shown in FIG. 4A, the ultrasound output unit 10 outputs high-intensity focused ultrasound (HIFU) of 3 W/cm² or above (Ispta) to apply a thermal or mechanical stimulus to a target focal point so that bone tissue in the focal point part is burned off or cut out. In an ideal embodiment, a thermal or mechanical stimulus that is equal to or higher than the threshold value (enough to destruct the bone tissue) is only generated at the target focal point on which an ultrasound beam is focused, to minimize damage to the human body at parts other than the target focal point or the ultrasonic wave pathway.

Figure 4B:
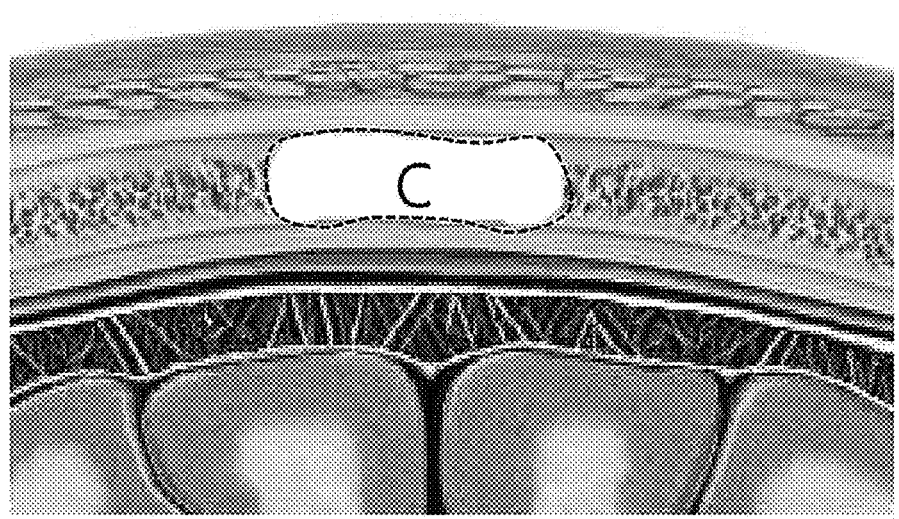

When the bone tissue is removed as described above, a cavity C is formed in the patient's skull as shown in FIG. 4B. According to embodiments, the user may incise the skull and remove the remaining bits, or extract the remaining bits using a syringe.

Figure 4C:
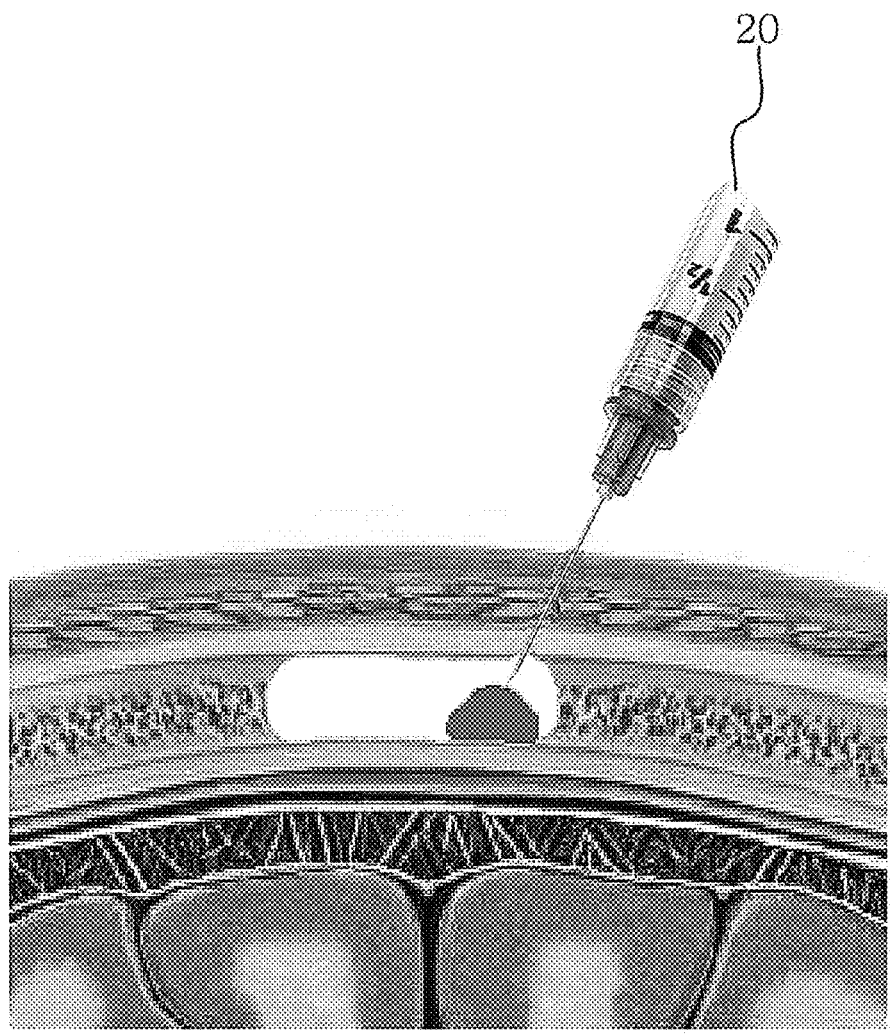

Subsequently, as shown in FIG. 4C, a medium is injected into the cavity C through the medium injection unit 20 to generate an intermedium. The medium injection unit 20 is a component that can inject a medium into the body with minimal invasion, such as a syringe.

As described above, the cavity in the skull may be filled with the medium to generate the intermedium that forms part of the treatment system. The intermedium may play different roles in the treatment system according to its material and properties. FIGS. 2 and 5-8 each show treatment methods according to the properties of the intermedium.

In FIG. 2, the acoustically-transparent intermedium M acting as an acoustic window is used. In this instance, the intermedium M may be made of a material having sound permeability such as amalgam or silicone, and therapeutic ultrasound may reach the patient's brain with minimized attenuation while passing through the intermedium.

The 'therapeutic ultrasound' includes all types of ultrasound used for treatment, for example, high-intensity focused ultrasound (HIFU) for directly cutting out or burning off lesions in the patient's body, low-intensity focused ultrasound (LIFU) for treating neurological disorders such as cognitive impairment, anxiety and depression by stimulating the brain with low intensity, and high frequency ultrasound for imaging the inside of the patient's body.

The therapeutic ultrasound may be outputted from the same ultrasonic transducer as high-intensity focused ultrasound for removing bone tissues, or may be outputted from a separate ultrasonic transducer. In an embodiment, a first transducer which outputs high-intensity focused ultrasound and a second transducer which outputs therapeutic ultrasound may be formed as devices in the shape of concentric circles, so each target focal point may be disposed on a straight line.

According to the above embodiment, it is possible to remove bone tissues in a desired site without directly incising the skull, and generate an acoustic window with minimal invasion using a syringe needle. Accordingly, it is possible to minimize the side effect (for example, infection of dura mater) caused by invasion, compared to the earlier technology having to incise the skull to insert an acoustic window.

According to an embodiment, after a plurality of acoustically-transparent intermedia is generated at a specific location, the lesion may be stimulated with higher intensity through an overlap of therapeutic ultrasound outputted from a plurality of sound sources.

Figure 9:
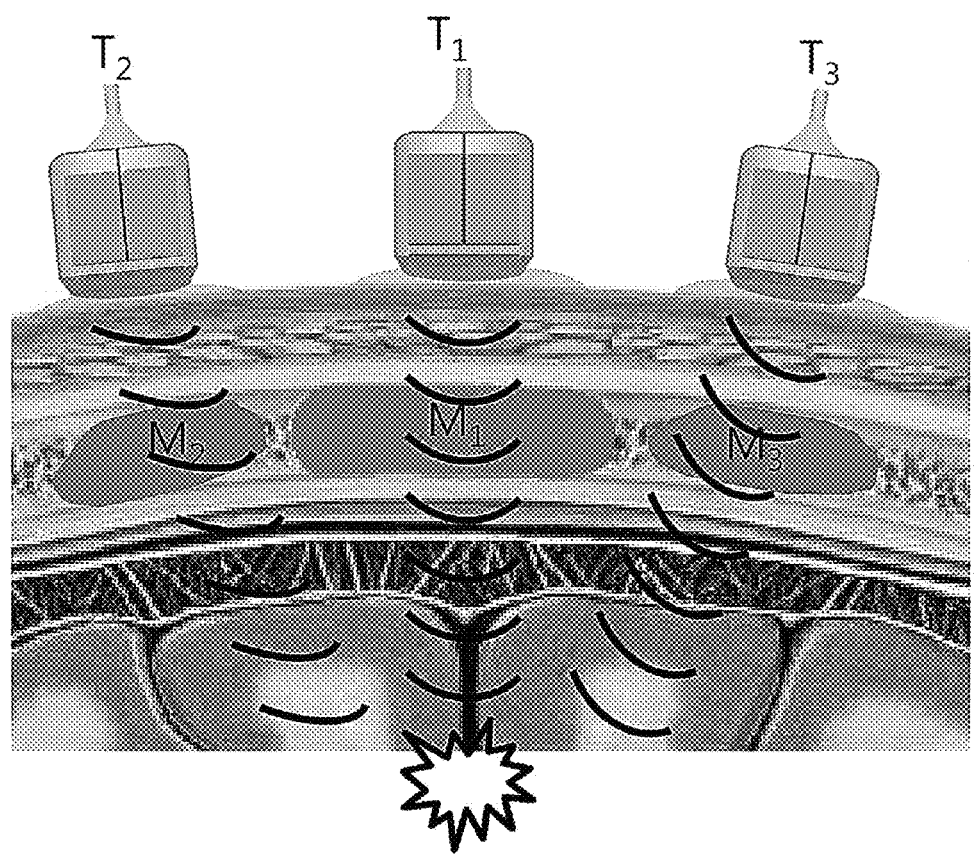
FIG. 9 shows an overlap of therapeutic ultrasound passing through a plurality of intermedia.

Referring to FIG. 9, each of bone tissues in many sites, not in one site, is removed using high-intensity focused ultrasound, and a sound permeable medium is injected into the part where the bone tissue is removed to form a plurality of acoustically-transparent intermedia $M_1$, $M_2$, $M_3$. The plurality of intermedia allows therapeutic ultrasound outputted from each of a plurality of ultrasound output elements $T_1$, $T_2$, $T_3$ to pass through, and delivers stimulation of the lesion more locally and deeply by concentration of a larger amount of energy through an overlap of therapeutic ultrasound.

The type of intermedium may be determined beforehand, taking into account each ultrasonic wave pathway and their overlap, and bone tissue removal and intermedia generation may be accomplished in a form that has been determined beforehand through an input from the high-intensity focused ultrasound output unit. Here, the overlap may refer to focusing onto a single target focal point, or constructive interference through an overlap of ultrasonic wave pathways.

Hereinafter, the embodiments of ultrasound treatment using intermedia M' made of materials having different properties will be described. The intermedium M of FIG. 2 acts as an acoustic window to allow therapeutic ultrasound to pass through the skull, while the intermedium M' described in the following embodiment may generate ultrasound itself by external induction (for example, incidence of light, application of voltage or generation of an electromagnetic field). To this end, the treatment device 1 may further include the ultrasound induction unit 30 including a light source to output light, a power source to apply voltage and a coil to generate an electromagnetic field.

Figure 5:
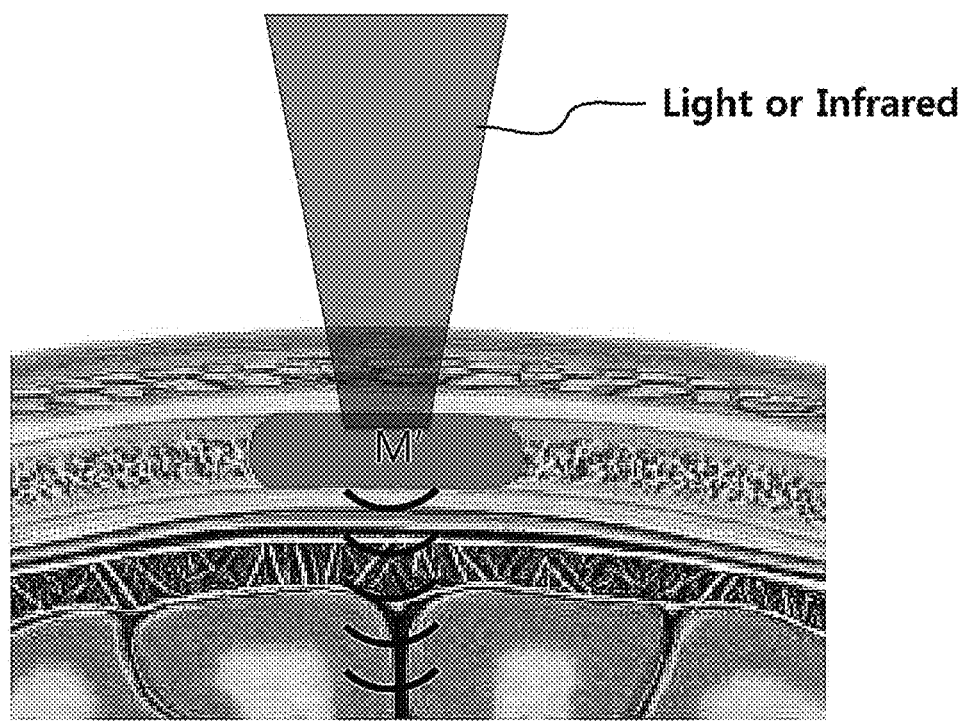
FIG. 5 shows ultrasound treatment using intermedium made of an opto-acoustic material.

FIG. 5 shows ultrasound treatment using intermedium made of an opto-acoustic material. The opto-acoustic effect is a phenomenon in which a material absorbs light and has the local temperature rise, and accordingly, the pressure propagates in the material, showing acoustic response, and using this, it is possible to capture medical images of human body tissues without any side effect by using the opto-acoustic material as a contrast agent.

The embodiment of FIG. 5 is a treatment method using the opto-acoustic effect. Specifically, bone tissue in the skull is removed using high-intensity focused ultrasound, and an opto-acoustic material is injected into the bone tissue removed site through the medium injection unit to generate an intermedium M'. The generated intermedium M' emits ultrasound into the patient's body when illuminated with light such as visible light, infrared light and laser. Using the ultrasound, medical images of the inside of the patient's body may be captured.

Figure 6:
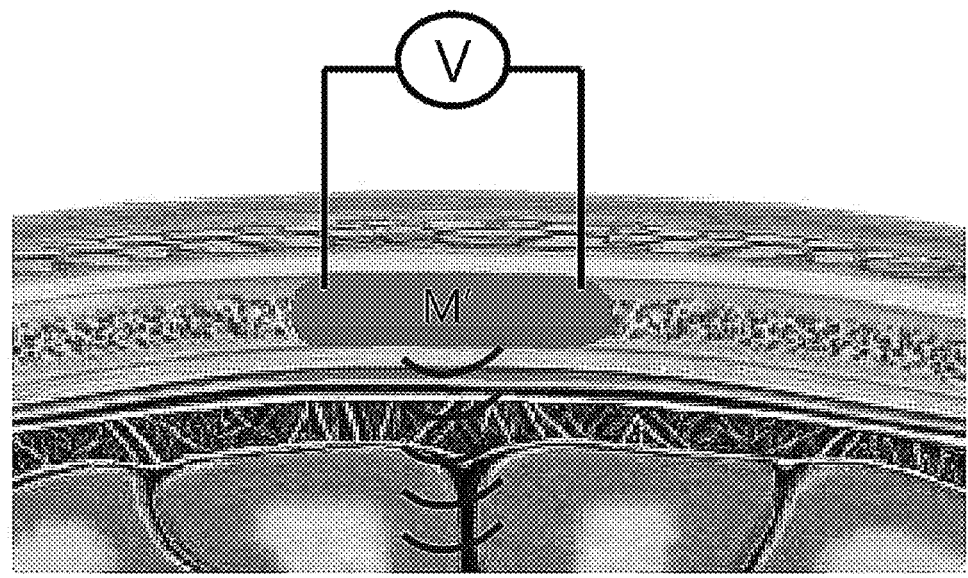
FIG. 6 shows ultrasound treatment using intermedium made of a piezoelectric material.

FIG. 6 shows ultrasound treatment using intermedium made of a piezoelectric material. A particular polymer material may exhibit acoustic response by strain or stress generated by an electric field, and on the contrary, may generate electric polarization by strain or stress, and this phenomenon is known as piezo-electricity.

The embodiment of FIG. 6 is a treatment method using the piezoelectric effect. Specifically, bone tissue in the skull is removed using high-intensity focused ultrasound, and a piezoelectric material is injected into the site where the bone tissue is removed through the medium injection unit to generate an intermedium M'. The generated intermedium M' may exhibit acoustic response in response to applied voltage. The method of applying voltage may be performed by inserting electrodes into the intermedium or by the electromagnetic induction method. Ultrasound generated from the intermedium M' may be used for direct treatment or imaging.

Figure 7:
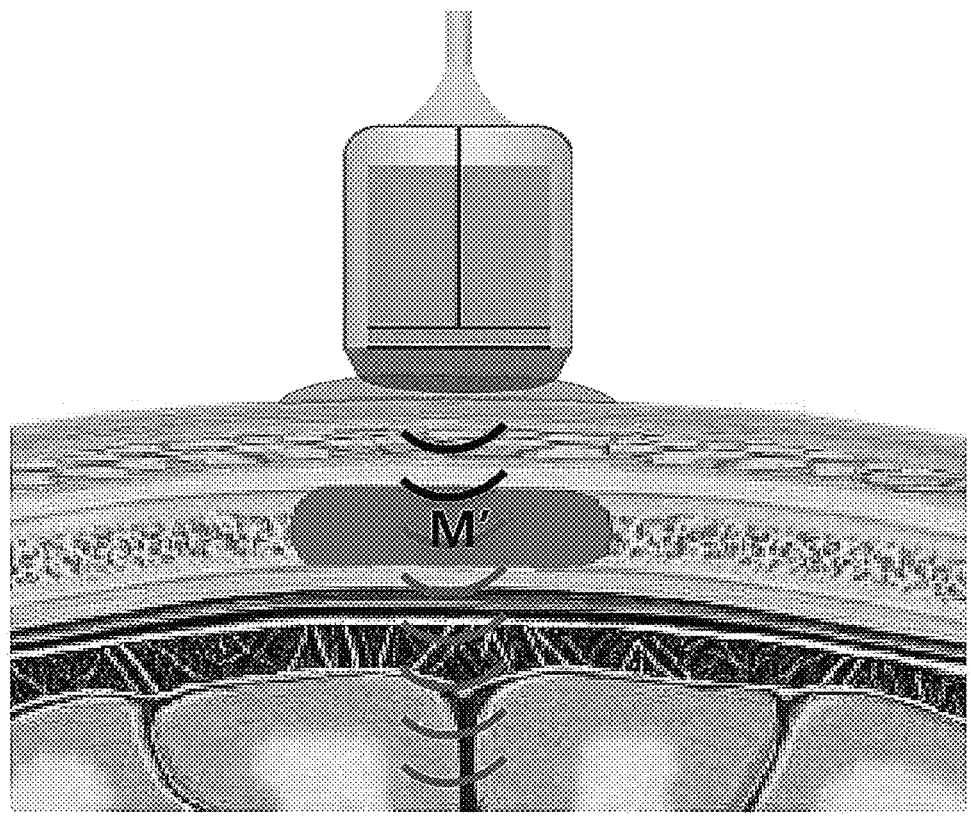
FIG. 7 shows ultrasound treatment using intermedium that acts as an ultrasound amplifier.

According to an embodiment, as shown in FIG. 7, the intermedium M' may be used as an acoustic amplifier to amplify the ultrasound outputted from the transducer. Also, in this case, similar to the embodiment of FIG. 6, the intermedium is formed from a piezoelectric material. To clarify the invention, a detailed description of the ultrasound amplification and emission principle of the intermedium made of a piezoelectric material is omitted herein.

Figure 8:
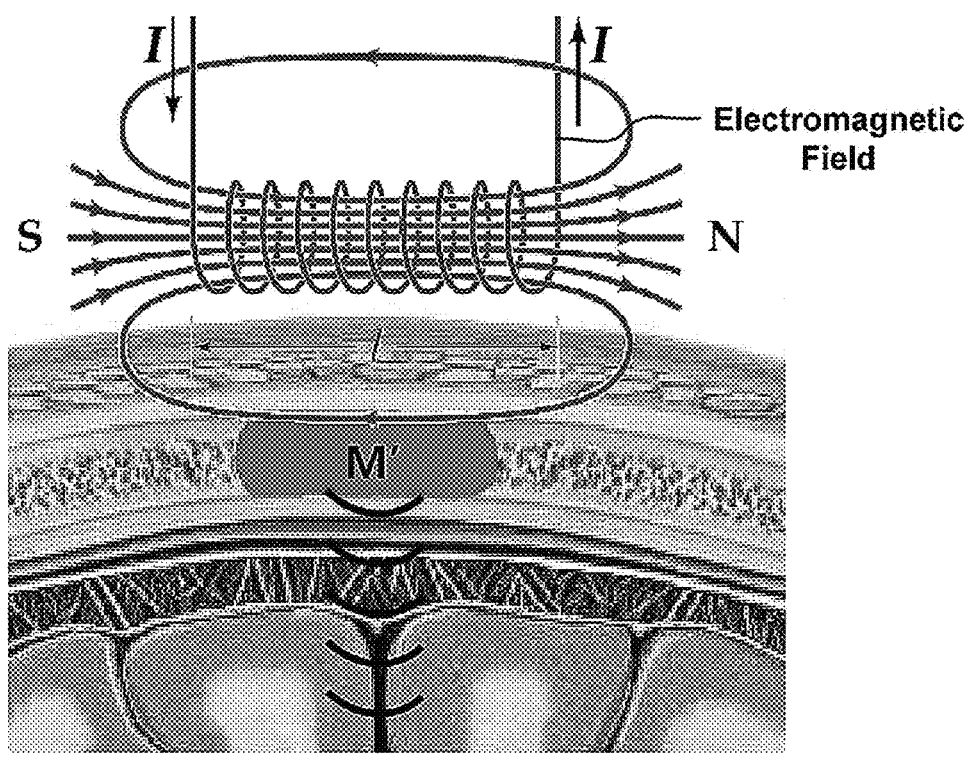
FIG. 8 shows ultrasound treatment using intermedium made of a ferroelectric material.

FIG. 8 shows ultrasound treatment using intermedium made of a ferroelectric material. The ferroelectric material is a material that has electric polarization in natural state and the polarization direction can be reversed by an electric field, and it has piezoelectric and pyroelectric properties by the spontaneous polarization reversal phenomenon. In an embodiment, the ferroelectric material that forms the intermedium M' may include, for example, yttrium-doped hafnium oxide (Y—HfO2), lead-zirconate-titanate composite compound (PZT) or low grade zinc oxide (HZO).

In the similar way to the above-described embodiments, bone tissue is removed using high-intensity focused ultrasound, and a ferroelectric material is injected into the empty site to generate the intermedium M'. As shown in FIG. 8, when the ultrasound induction unit generates an electromagnetic field, the ferroelectric intermedium M' emits ultrasound accordingly. Likewise, ultrasound emitted from the intermedium M' may be used for direct treatment or imaging.

The control unit 40 may include a combination of a series of software and hardware that controls the operation of the ultrasound output unit 10 or the other components of the system. For example, the control unit 40 may control the parameters such as the target focal point, intensity and frequency of focused ultrasound and therapeutic ultrasound outputted from the ultrasound output unit, or mechanically operate each device or array of the ultrasound output unit. The control unit is a concept that encompasses software/hardware components therefor, such as a computer processor, a transmission/reception circuit and a motor driving device. The control unit may control the operation of the ultrasound output unit 10 as well as devices that make up the medium injection unit 20 or the ultrasound induction unit 30.

According to the non-invasive treatment system described above, the bone tissue is removed in a non-invasive way using high-intensity focused ultrasound, and the intermedium is generated at the part where the bone tissue is removed, to increase the penetration of therapeutic ultrasound or generate ultrasound itself, thereby improving the ultrasound treatment effect while minimizing the side effect (for example, infection of dura mater) of the invasive surgery methods. Although skull and brain treatments are primarily described herein, the treatment system will be equally applied to all human body parts requiring ultrasound treatment.

While the present disclosure has been hereinabove described with reference to the embodiments, it will be understood by those having ordinary skill in the corresponding technical field that various modifications and changes may be made to the present disclosure without departing from the spirit and scope of the present disclosure as defined by the appended claims.

What is claimed is:

1. A non-invasive ultrasound treatment system comprising:
   a first ultrasound transducer configured to output high-intensity focused ultrasound to a target focal point spaced from a skin of a patient to remove bone tissue of the patient at the focal point while being spaced from the patient to form a cavity in a skull of the patient;
   a syringe configured to inject a medium into a part of the patient where the bone tissue is removed to generate an intermedium; and
   a second ultrasound transducer configured to output therapeutic ultrasound that passes through the patient then through the intermedium, the intermedium being configured to amplify the outputted therapeutic ultrasound.

2. The non-invasive ultrasound treatment system according to claim 1, wherein the therapeutic ultrasound includes high-intensity focused ultrasound (HIFU), low-intensity focused ultrasound (LIFU), or high frequency ultrasound for imaging.

3. The non-invasive ultrasound treatment system according to claim 1, wherein the intermedium includes a plurality of intermedia generated at preset locations, and
   the plurality of intermedia allows therapeutic ultrasound outputted from each of a plurality of ultrasound output elements to pass through, and the therapeutic ultrasound is configured to stimulate a lesion of the patient with higher intensity through an overlap.

4. A non-invasive ultrasound treatment system, comprising:
   a first ultrasound transducer configured to output high-intensity focused ultrasound to a target focal point spaced from a skin of a patient to remove bone tissue of the patient at the focal point while being spaced from the patient to form a cavity in a skull of the patient;
   a syringe configured to inject a medium into a part of the patient where the bone tissue is removed to generate an intermedium that can generate ultrasound itself by external induction; and
   a second ultrasound transducer configured to induce the intermedium to generate the ultrasound.

5. The non-invasive ultrasound treatment system according to claim 4, wherein the intermedium is made of an opto-acoustic material that generates ultrasound by incident light, and
   the ultrasound treatment system is further configured to generate light to the intermedium.

6. The non-invasive ultrasound treatment system according to claim 4, wherein the intermedium is made of a piezoelectric material that generates ultrasound by applied voltage, and
   the ultrasound treatment system is further configured to apply voltage to the intermedium.

7. The non-invasive ultrasound treatment system according to claim 4, wherein the intermedium acts as an amplifier to amplify received ultrasound, and
   the ultrasound treatment system is further configured to output ultrasound to the intermedium.

8. The non-invasive ultrasound treatment system according to claim 4, wherein the intermedium is made of a ferroelectric material that generates ultrasound by a change in electromagnetic field, and
   the ultrasound treatment system is further configured to generate an electromagnetic field.

9. A non-invasive ultrasound treatment device, comprising:
   a first ultrasound transducer configured to output a high-intensity focused ultrasound to a target focal point spaced from a skin of a patient to remove bone tissue of the patient at the focal point while being spaced from the patient to form a cavity in a skull of the patient;
   a syringe configured to inject a medium into a part of the patient where the bone tissue is removed to generate an intermedium; and
   a controller configured to control operation of the first ultrasound transducer, including the target focal point, intensity of the high-intensity focused ultrasound, and frequency of the high-intensity focused ultrasound.

10. The non-invasive ultrasound treatment device according to claim 9, wherein the intermedium is made of an acoustically-transparent material, and
    the first ultrasound transducer further outputs therapeutic ultrasound that passes through the intermedium.

11. The non-invasive ultrasound treatment device according to claim 10, wherein the intermedium includes a plurality of acoustically-transparent intermedia generated at preset locations,
    the first ultrasound transducer includes a plurality of ultrasound output elements corresponding to the plurality of acoustically-transparent intermedia, and
    the plurality of acoustically-transparent intermedia allows therapeutic ultrasound outputted from each of the plurality of ultrasound output elements to pass through, and the therapeutic ultrasound stimulates a lesion with higher intensity through an overlap.

12. The non-invasive ultrasound treatment device according to claim 9, wherein the intermedium is made of a material that can generate ultrasound itself by external induction, and
    the ultrasound treatment device further comprises a second ultrasound transducer to induce the intermedium to generate ultrasound.

13. The non-invasive ultrasound treatment device according to claim 12, wherein the intermedium is made of an opto-acoustic material that generates ultrasound by incident light.

14. The non-invasive ultrasound treatment device according to claim 12, wherein the intermedium is made of a piezoelectric material that generates ultrasound by applied voltage, and
    the second ultrasound transducer applies voltage to the intermedium.

15. The non-invasive ultrasound treatment device according to claim 12, wherein the intermedium acts as an amplifier to amplify received ultrasound, and
    the second ultrasound transducer outputs ultrasound to the intermedium.

16. The non-invasive ultrasound treatment device according to claim 12, wherein the intermedium is made of a ferroelectric material that generates ultrasound by a change in electromagnetic field, and
    the second ultrasound transducer generates an electromagnetic field.

17. The non-invasive ultrasound treatment device according to claim 9, wherein the first ultrasound transducer uses a piezoelectric material, is a capacitive micromachined ultrasonic transducer (CMUT), is a piezoelectric micromachined ultrasonic transducer (PMUT), uses an opto-acoustic effect, or uses an electromagnetic force.

* * * * *